United States Patent
Blomster et al.

(10) Patent No.: US 7,088,437 B2
(45) Date of Patent: Aug. 8, 2006

(54) OPTICAL FIBRE MEANS

(75) Inventors: Ola Blomster, Onsala (SE); Sven-Olov Roos, Lerum (SE)

(73) Assignee: Optoskand AB, Mölndal (SE)

( * ) Notice: Subject to any disclaimer, the term of this patent is extended or adjusted under 35 U.S.C. 154(b) by 0 days.

(21) Appl. No.: 10/486,686

(22) PCT Filed: Aug. 9, 2002

(86) PCT No.: PCT/SE02/01441

§ 371 (c)(1),
(2), (4) Date: Aug. 26, 2004

(87) PCT Pub. No.: WO03/016854

PCT Pub. Date: Feb. 27, 2003

(65) Prior Publication Data

US 2005/0013525 A1    Jan. 20, 2005

(30) Foreign Application Priority Data

Aug. 15, 2001   (SE) .................................... 0102718

(51) Int. Cl.
*G01N 21/00* (2006.01)
(52) U.S. Cl. ................................................... 356/73.1
(58) Field of Classification Search ............... 356/73.1; 385/88–91, 24

See application file for complete search history.

(56) References Cited

U.S. PATENT DOCUMENTS

| 4,192,995 A | 3/1980 | Anthon |
| 4,385,832 A | 5/1983 | Doi et al. |
| 4,556,875 A | 12/1985 | Ishiwatari |
| 4,812,641 A | 3/1989 | Ortiz, Jr. |
| 5,497,442 A | 3/1996 | Roos et al. |
| 6,547,453 B1 * | 4/2003 | Stummer et al. ............. 385/88 |

FOREIGN PATENT DOCUMENTS

| DE | 4032967 A1 | 4/1991 |
| EP | 0506401 A2 | 9/1992 |
| EP | 0844472 B1 | 5/1998 |

* cited by examiner

*Primary Examiner*—Tu T. Nguyen
(74) *Attorney, Agent, or Firm*—Venable LLP; Eric J. Franklin

(57) ABSTRACT

The present invention relates to a method and a device for detecting damages in an optical fibre (1,2) made for transmitting high optical power, specifically power exceeding 1 kW, and where the optical fibre (1,2) has an entrance end (7) for incident optical radiation (4) and an exit end where the optical radiation is leaving the fibre. According to the invention substantially radially spread radiation in connection with the entrance and/or exit parts of the fibre is detected, and if this radiation exceeds a certain level this is used as an indication of a damage in the entrance and/or exit zone of the fibre.

10 Claims, 1 Drawing Sheet

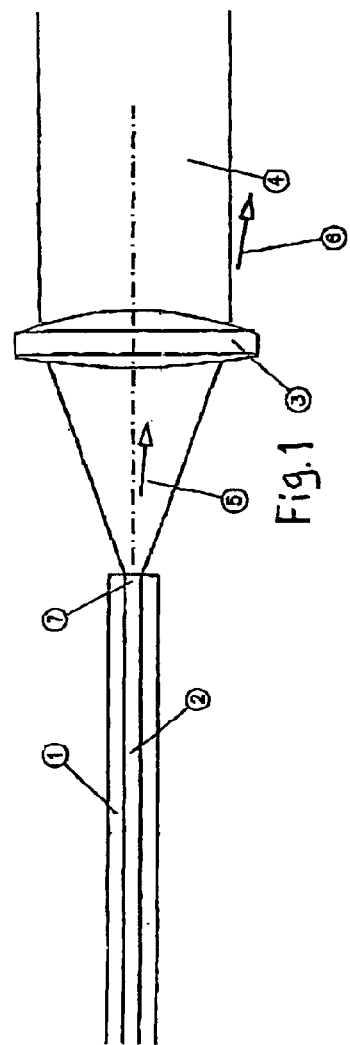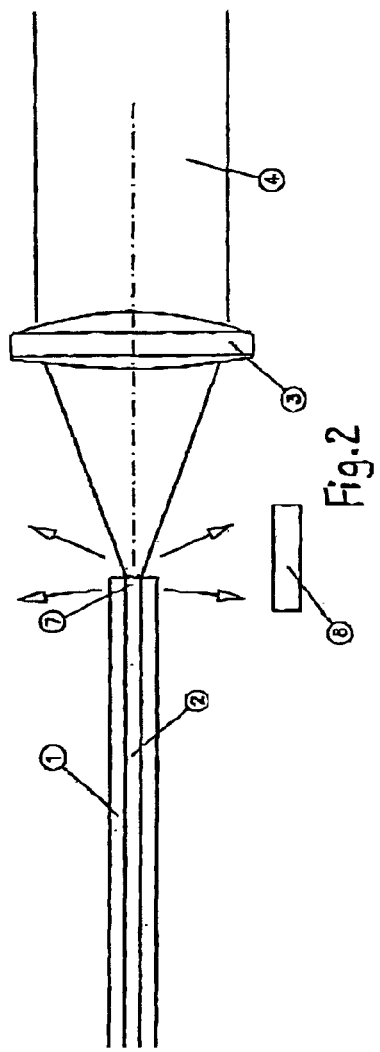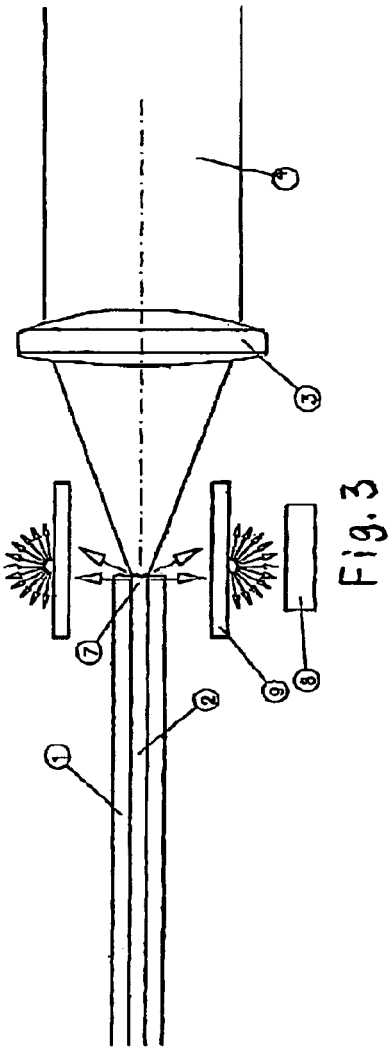

OPTICAL FIBRE MEANS

CROSS-REFERENCE TO RELATED APPLICATIONS

This application claims priority from Swedish patent application 0102718-4 filed 15 Aug. 2001 and is the National Phase under 35 U.S.C. §371 of PCT/SE02/01441.

FIELD OF THE INVENTION

The present invention relates to a method and a device for detecting damages in an optical fibre made for transmitting high optical power, specifically power exceeding 1 kW, and where the optical fibre has an entrance end for an incident optical beam and an exit end where the optical beam is leaving the fibre.

BACKGROUND OF THE INVENTION

Optical fibres for transmitting high optical power are frequently used in industrial applications. Specifically they are used in cutting and welding operations by means of high-power laser radiation, but also in other industrial applications such as heating, detection or working operations in high-temperature environments this type of optical fibres can be used. By means of the optical fibres it is possible to design flexible manufacturing systems for transmitting the laser beam from the high power laser source to the workpiece. An optical fibre typically has an inner glass core and a surrounding layer, a so-called cladding, having a lower refractive index than the glass core. The function of the cladding is to keep the optical beam to the core. Laser sources which can be used in this context have an average power from a few hundred watts up to several kilowatts.

When designing fibre systems for such high power laser radiation it is important that the fibre is not damaged in any way because the radiation from a "leaking" or damaged fibre might cause serious personal injuries. Therefore it is previously known to check the status of the fibre by means of specific monitoring systems. See for instance U.S. Pat. Nos. 4,812,641, DE 4032967, DE 3246290, DE 3031589 and U.S. Pat. No. 5,497,442.

However, it is important to detect a damage in the optical fibre not only for security reasons but also for preventing secondary damages in other parts of the system due to said damages or imperfections in the fibre.

A weakness in all of the detecting systems referred to above is the fact that the detection of a damage comes too late. When the radiation from the damaged fibre is detected, secondary damages in the optical system might already have occured.

SUMMARY OF THE INVENTION

The object of this invention is to provide a method and a device for detecting a possible damage in an optical fibre at an early stage, in order to avoid any secondary damages in the optical system.

The invention is based on the knowledge that it is the entrance or the exit part of the fibre that is damaged first. This is true because it is these parts of the fibre that are most exposed to the radiation. Normally there are some reflection losses at the fibre ends, but this radiation is then substantially coaxial with the longitudinal direction of the fibre. In case of a damage in the entrance or exit part of the fibre there is also a spread radiation more or less in the radial direction of the fibre.

According to the invention this substantially radial radiation is detected and a certain level of the radiation indicates that there is a damage in the entrance or exit part of the fibre.

Specifically, the invention is characterized by a photo detector arranged to detect radiation that is spread substantially in a radial direction from the entrance and/or exit ends of the fibre.

According to a preferred embodiment the spread radiation is arranged to hit a diffusor surface before it hits the detector.

BRIEF DESCRIPTION OF THE DRAWINGS

In the following the invention will be described more in detail with reference to the accompanying drawings in which FIG. 1 schematically illustrates an optical fibre system in which the radiation is focused to the core of the fibre and with no damage in the fibre, FIG. 2 illustrates the optical fibre system in case of a damage in the entrance part of the fibre and a resulting spread radiation subtantially in a radial direction from the fibre, and FIG. 3 shows the optical fibre system with detecting means according to the invention.

DETAILED DESCRIPTION OF EMBODIMENTS OF THE INVENTION

FIG. 1 illustrates one end 7 of a conventional optical fibre having a core 2, for example of quartz glass, and a surrounding cladding 1 with a lower refractive index than the glass core, for example made of glass or some polymer having a suitable refractive index. The function of the cladding is to keep the radiation in the core so that the radiation is transmitted through the fibre in its longitudinal direction until it leaves the fibre on the exit surface (not shown).

Outside the cladding 1 of the fibre there are normally further layers arranged in order to, among other things, improve the mechanical strength of the fibre. However, these layers are not illustrated here as they are known per se and not required to explain the idea of the present invention.

The radiation, for instance in the form of a laser beam 4, is focused on the end surface 7 of the fibre by means of optics in the form of one or more lenses 3 or mirrors. Normally there are some reflection losses in the fibre ends as well as in the optics, which have been indicated by the arrows 5 and 6 in the figure. This radiation is then substantially coaxial with the longitudinal direction of the fibre.

The laser beam 4 which is focused on the end surface of the fibre could be of any known type. For instance a NdYAG laser source is used which has a wave-length of 1.06 μm. This wave-length is suitable for optical fibre transmission. Other examples of lasers that can be used is diode lasers, $CO_2$-lasers, CO-lasers and other types of YAG lasers.

Common for said types of laser radiation is the high optical power which might cause injuries to personnel as well as damages in the optical system if the radiation is not correctly transmitted through the fibre. Even a small imperfection in the fibre can become critical and cause serious personal injuries as well as material damages.

That part of the fibre which is most exposed to radiation is the entrance part 7 and consequently it is often here that damages could be found. These damages give rise to a spread radiation also in a more or less radial direction from the fibre as illustrated in FIG. 2. By providing a photo detector 8 to sense this radiation, damages in the fibre entrance part 7 can be detected.

The detector 8 can be arranged to sense this radiation directly or indirectly by means of a transparent diffuser 9, see FIG. 3. By using a diffuser the signal will be less sensitive to the directivity of the radiation, i e less sensitive to the main direction of the spread radiation.

Suitable detectors for measuring the radial radiation could be photo diodes, which could be used in both photo voltaic and photo conductive modes.

The detector 8 is preferably arranged in connection with the entrance part of the fibre as illustrated in FIGS. 2 and 3, but it can also be arranged on a certain distance from this end in which case the radiation is transmitted via optics to the detector.

In the examples which have been illustrated here the detector 8 has been arranged in connection with the entrance part 7 of the fibre. It should be understood, however, that the detector in the same way could be arranged in connection with the exit part of the fibre, as also this zone is exposed to damages from the radiation. Alternatively, the entrance zone as well as the exit zone could be arranged with detectors for sensing radial radiation.

The invention claimed is:

1. A method for detecting damages in an optical fiber made for transmitting high optical power, where the optical fiber has an entrance end for incident optical radiation and an exit end where the optical radiation is leaving the fiber, the method comprising:
    detecting substantially radially reflected radiation from said incident optical radiation in the vicinity of at least one of the entrance or exit parts of the fiber, and
    if the substantially radially reflected radiation exceeds a certain level this is used as an indication of a damage in the vicinity of at least one of the entrance or exit parts of the fiber.

2. The method according to claim 1 wherein the radially reflected radiation is arranged to hit a diffuser surface before it is detected.

3. The method according to claim 1, wherein the optical fiber is made for transmitting high optical power exceeding 1 kW.

4. A device for detecting damages in an optical fiber made for transmitting high optical power, where the optical fiber has an entrance end for incident optical radiation and an exit end where the optical radiation is leaving the fiber, the device comprising:
    a detector for sensing substantially radially reflected radiation from said incident optical radiation in the vicinity of at least one of the entrance or exit parts of the fiber, and if this sensed radiation exceeds a certain level this is used as an indication of a damage in at least one of the entrance or exit parts of the fiber.

5. The device according to claim 4 wherein a diffusor surface arranged in front of the detector.

6. The device according to claim 5 wherein the diffusor surface is transparent.

7. The device according to claim 5 wherein the diffusor surface is reflecting.

8. The device according to claim 4 wherein the detector is arranged in the vicinity of at least one of the entrance end or the exit end of the fiber.

9. The device according to claim 4 wherein the detector is arranged at a distance from at least one of the entrance or exit end of the fiber, the device further comprising:
    optics operative to transmit the radially reflected radiation to the detector.

10. The device according to claim 4, wherein the optical fiber is made for transmitting high optical power exceeding 1 kW.

\* \* \* \* \*